United States Patent [19]
Stanitzok

[11] Patent Number: 5,439,487
[45] Date of Patent: Aug. 8, 1995

[54] DEVICE FOR COSMETICALLY PEELING THE SKIN

[76] Inventor: Horst Stanitzok, Rosastr. 1, 79098 Freiburg, Germany

[21] Appl. No.: 198,881

[22] Filed: Feb. 17, 1994

[51] Int. Cl.$^6$ ................................................. A47K 7/02
[52] U.S. Cl. ........................................ 15/227; 15/208; 15/209.1; 139/420 A; 139/426 R; 428/224; 428/225; 428/229; 428/253
[58] Field of Search ............... 428/224, 225, 229, 253; 139/420 A, 426 R; 15/208, 209.1, 227

[56] References Cited
U.S. PATENT DOCUMENTS
4,091,491  5/1978  Hoffman .
4,932,095  6/1990  Kawase .

FOREIGN PATENT DOCUMENTS
0086355  8/1983  European Pat. Off. .
1802174  4/1970  Germany .
2402887  7/1974  Germany .

Primary Examiner—James J. Bell
Attorney, Agent, or Firm—Robert W. Becker & Associates

[57] ABSTRACT

A device for cosmetically peeling skin with a textile fabric has a textile fabric made of filament yarns or spun yarns that consist of synthetic fibers or silk fibers. The yarn preferably has a structure that is twisted, textured, or twisted/textured. The fibers preferably have a size of less than 3 dtex and the yarns preferably have a size of less than 30 tex. The device may be in the form of a glove, a washcloth, a brush, or a pad.

19 Claims, 1 Drawing Sheet

DEVICE FOR COSMETICALLY PEELING THE SKIN

BACKGROUND OF THE INVENTION

The present invention relates to a device for cosmetically peeling the skin with a textile fabric.

The cosmetic removal of skin, for example, of facial skin or body skin, is generally, called peeling. In the following this term will be used. Peeling, in general, relates to the surficial removal of dead skin particles.

For mechanically peeling the skin it is conventional to use special creams or ointments that contain granular grinding materials. Upon rubbing the cream on to the skin the creams loosen individual dead skin particles and/or grind them up at the particular location of application. It is disadvantageous that the desired peeling effect cannot be achieved to the optimal extent, especially since the creams during the peeling process do not allow visual monitoring whether the peeling effect has been achieved to the desired extent. It is furthermore disadvantageous that the desired peeling effect cannot be achieved without the risk of skin irritation or injury by abrasion.

A device for cosmetically peeling the skin of the aforementioned kind is known from U.S. Pat. No. 4,091,491. A so-called peeling glove is provided which as a peeling-effecting surface has a textile fabric made of a coarse fabric, such as sail cloth or denim. These fabrics do result in a peeling effect; however, they are not very effective. The prior art peeling glove primarily has the effect of a massage glove due to its noticeable strong scratching effect.

It is therefore an object of the present invention to provide an improved device for cosmetically peeling the skin by using a textile fabric.

BRIEF DESCRIPTION OF THE DRAWINGS

This object, and other objects and advantages of the present invention, will appear more clearly from the following specification in conjunction with the accompanying drawings, in which.

SUMMARY OF THE INVENTION

Figure 1:
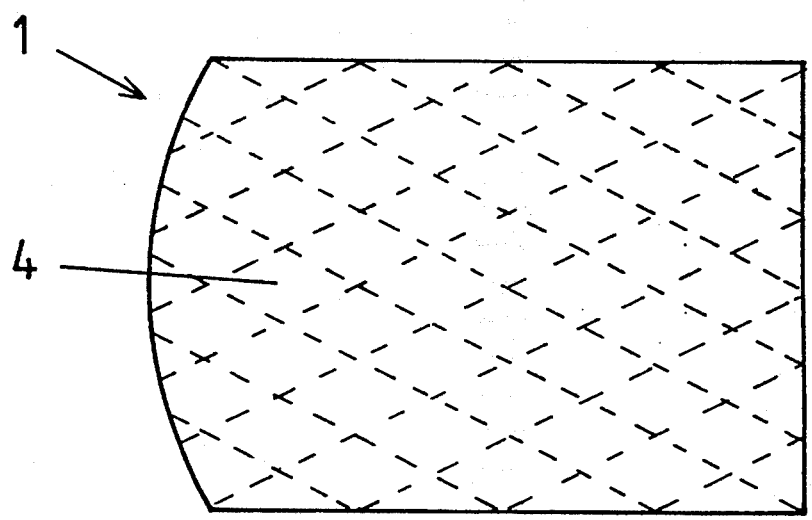
FIG. 1 shows a plan view of the inventive glove.

The device for cosmetically peeling skin with a textile fabric according to the present invention is primarily characterized by:

A textile fabrics of yarns selected from the group consisting of filament yarn and spun yarn made of fibers selected from the group consisting of synthetic fibers and silk fibers;

The yarn having a structure selected from the group consisting of twisted, textured, and twisted/textured; and The fibers having a size of less than 3 dtex; and
The yarn having a size of less than 30 tex.

Preferably, the textile fabric is selected from the group consisting of a woven fabric, a knit fabric, and a non-woven fabric;

Advantageously, the textile fabric has a weave selected from the group consisting of linen weave, filling-satin weave, and crepe weave. Preferably, the filling-satin weave has a small repeat.

Advantageously, the yarn has more than 1,000 twists per meter. Preferably, the yarn has substantially 2,000 to 2,400 twists per meter.

In a preferred embodiment of the present invention, the textile fabric is comprised of first yarns and second yarns, the first yarns having a different direction of twisting than the second yarns. Preferably, the first yarns are twisted at a change sequence of 1/1 and the second yarns are twisted at a change sequence of 2/2.

Advantageously, the size of the fibers is less than 1.8 dtex, preferably between 1.0 to 1.2 dtex.

Advantageously, the size of the yarn is less than 20 tex, preferably less than 10 tex. Most advantageously, the size of the yarn is between 0.1 and 5.0 tex.

The unit of measure "tex" is defined as the mass of one kilometer of the yarn material. The unit of measure "dtex" is a decitex or one tenth of a tex.

In a preferred embodiment of the present invention the device further comprises a backing to which backing the textile fabric is attached. Preferably, the backing is soft and elastic. Advantageously, the textile fabric is quilted onto the backing in a diamond pattern. Preferably, the diamond pattern is comprised of diamonds of a side length of 1.0 to 1.5 cm.

In a preferred embodiment of the present invention the device is embodied as a hand-held apparatus selected from the group consisting of a washcloth, a glove, a pad, and a brush.

With the inventive textile fabric device a simple and effective method for peeling the skin on large areas is provided. Since the textile fabric due to its construction has a certain surface roughness, a scrubbing effect results due to this peeling-effective surface so that the dead particles of the skin can be easily removed. The peeling effect thus results from the special and innovative construction of the surface of the textile fabric. According to the present invention a finely structured, diffuse surface area with a substantially "chaotic" (irregular) structure is provided which ensures the desired surface roughness. It is essential in this context to realize that the peeling effect is most effective on moist or wet, presoaked skin in combination with a moist textile fabric. The peeling effect is reduced upon increasing the degree of moisture of the textile fabric and can therefore be adjusted. When the skin as well as the textile fabric are both dry, only a very small peeling effect is observed; the textile fabric is then to be used for a daily massage regimen. The material selected for the textile fabric is preferably a synthetic fiber, especially polyester, or, in the alternative, silk. It is, for example, possible that the synthetic fibers are provided with a cross-sectional texture, i.e., they do not have a circular cross-section. It is also possible to use plastic film strips as the fiber material which film strips are correspondingly twisted. The surface roughness of the textile fabric can be attained by different factors of the fine yarn surface structure of the fabric in the form of a woven or non-woven or knit fabric. This will be explained in detail in the following, Inasmuch as the filament yarn or filament thread is provided with a twist, the state of the yarn/thread at the surface is the determining factor because only this surface is of importance for the peeling effect. The use of continuous filaments has the advantage that the filament yarn and thus the textile fabric cannot mat and that therefore a transverse orientation of the filaments provided at the peeling-effective fabric surface is always ensured. The fiber material is preferably either synthetic fibers or silk. With silk fibers of a fine size or commercial filament yarns with a smooth fiber structure very good peeling effects are attainable.

The textile fabric may be a woven fabric or a nonwoven fabric or a knit fabric. Preferably, the textile fabric is a fabric with which the best peeling effects can be achieved. The fabric is a so-called fine fabric which has the required surface properties according to the present invention with respect to fiber size, yarn size, twisting and crimping of the yarn, as well as effectiveness of the fiber orientation (different twisting direction as well as diffuse (irregular) appearance) for attaining the desired peeling effect. If instead of the woven fabric a knit or non-woven fabric is used, this knit fabric or nonwoven fabric must have the same properties as the fine fabric in order to provide the desired peeling effect in an equivalent manner.

The type of weave has also an important effect on the peeling effect. Weaves in which the warp and/or weft are provided with a greatest possible curvature at the surface of the fabric are especially suitable for the peeling effect than fabrics with yarns that are floating on the surface of the fabric. For the peeling of the skin especially those fabrics are suitable that, pursuant to a further embodiment of the invention, have a linen weave, a filling-satin weave, preferably with a small repeat, or a crepe weave. The best results in regard to the peeling effect can be reached with a weave construction of a linen weave ( L 1/1). However, filling-satin weaves with a small repeat as well as crepe weaves are also suitable. Ideal conditions for a crepe weave are obtainable with highly twisted warp and weft yarns woven with a linen weave. Crepe weaves are characterized by the typical irregular positioning of the individual warp and weft yarns.

Very good peeling results are obtained with crepe weaves made of polyester. These fabrics exhibit in the wet state an even rougher surface, i.e., a higher scrubbing effect, than silk crepe fabrics. A still satisfactory peeling effect is obtained, however, in a slightly reduced form, when in the weaving direction crepe yarns with different twisting directions are used and when these are mostly arranged at the surface of the fabric.

Preferably, the twisted filament yarn has more than 1,000 twists per meter, especially substantially 2,000 to 2,400 twists per meter. Advantageously, the use of these highly twisted yarns result in a satisfactory peeling effect. Below the given range a satisfactory peeling effect can no longer be obtained or is too small. For twisting above 1,300 twists per meter, good peeling effects are attained whereby the optimal range is between 2,000 and 2,400 twists per meter.

In a further embodiment it is suggested that for the textile fabric filament yarns of different twisting directions, especially in the change sequence 1/1 or 2/2, are used. The peeling effect is the lowest for warp and weft yarns of the same twisting direction, while the peeling effect is the greatest when the yarns, which form the warp and weft yarns of the fabric, have different twisting directions, especially with a change sequence 1/1 or 2/2. The twisting direction of the yarns has thus an important influence on the peeling effect. For example, in the warp direction the warp yarns may alternatingly have a Z-twist or an S-twist or vice versa, while in the weft direction two yarns with S-twist and two yarns with Z-twists should be provided alternatingly. Of course, different combinations are possible. It is, however, a decisive factor that the different rotational directions are provided at the peeling-effective surface of the fabric.

Preferably, the fiber size is below 1.8 dtex, especially between 1.0 and 1.2 dtex. With such a fiber or filament size the best peeling effects are observed.

Preferably, the yarn size is below 20 tex, preferably below 10 tex and more preferred 0.1 and 5.0 tex. Especially within the last named size range very good peeling effects are observed. For example, raw silk, with which a very good peeling effect can be attained, has a yarn size of approximately 2.3 tex.

In a further embodiment of the inventive device for cosmetically peeling the skin it is suggested that the textile fabric be attached to a backing. With such a backing, the textile fabric is provided with a required stability and is thus easy to handle.

Preferably, the backing is soft and elastic and thereby further increases the peeling effect of the textile fabric attached to the backing.

Furthermore, it has been shown that, when the textile fabric for peeling is only loosely attached to the backing, a low peeling effect is achieved. For this reason, in another embodiment it is suggested that the textile fabric is quilted in a diamond pattern onto the backing, whereby the diamonds of the pattern preferably have a side length of 1 to 1.5 cm. Of course, it is also possible to attach the textile fabric in any other suitable manner to the backing, for example, in a circular quilting pattern etc.

In a further embodiment of the present invention it is suggested that the inventive device for cosmetically peeling the skin is in the shape of a Glove, a washcloth, a pad, a brush or any other suitable shape or body. This will ensure a simple handling and manipulation of the inventive device for peeling the skin whereby the textile fabric that achieves the peeling effect is attached to a Glove, a washcloth, a pad or brush body. The pads may be disk-shaped and may have a diameter of approximately 5 cm.

DESCRIPTION OF PREFERRED EMBODIMENTS

The present invention will now be described in detail with the aid of several specific embodiments utilizing FIGS. 1 and 2.

Figure 2:
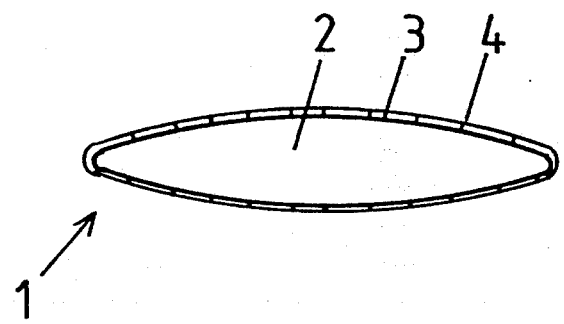
FIG. 2 shows a section along the line II—II of FIG. 1.

The device for cosmetically peeling the skin is represented in FIG. 1 in the form of a glove 1 made of cotton terrycloth, into which the user in the conventional manner inserts his hand through the opening 2. The glove 1 represents the soft and elastic backing 3 for the textile fabric 4 that is quilted with a diamond pattern onto the backing 3.

The textile fabric for the peeling effect is preferably a crepe fabric with 110 warp yarns per centimeter and 35 weft yarns per centimeter. The warp is preferably made of Z-twist and S-twist warp yarns alternatingly arranged in the warp. Preferably, a double-twisted yarn made of raw silk of a size of 2.3 tex with a twist number of approximately 2,300 per meter is used. In the weft direction the same yarn is used. However, two weft yarns with an S-twist and two weft yarns with a Z-twist are employed alternatingly.

The textile fabric has the typical irregular appearance of a crepe fabric with regard to the individual warp and weft yarns, i.e., due to the alternating S and Z twists the fabric surface is irregular. The yarn orientation at the fabric surface differs greatly with respect to its angle of incline and is thus oriented in a diffuse manner.

The peeling glove 1 embodied as described above functions as follows:

The skin to be peeled is first wetted and presoaked. The glove 1 and especially the textile fabric 4 is also wetted. Subsequently, the user rubs the skin with the textile fabric 4 of the glove 1.

The present invention is, of course, in no way restricted to the specific disclosure of the specification and drawings, but also encompasses any modifications within the scope of the appended claims.

WHAT I CLAIM IS:

1. A skin-care device for cosmetically peeling skin embodying a hand-held apparatus comprising
   a textile fabric, said textile fabric comprised of yarns selected from the group consisting of filament yarn and spun yarn made of fibers selected from the group consisting of synthetic fibers and silk fibers;
   said yarn having a structure selected from the group consisting of twisted, textured, and twisted/textured;
   said fibers having a size of less than 3 dtex;and
   said yarn having a size of less than 30 tex.

2. A device according to claim 1, wherein said textile fabric is selected from the group consisting of a woven fabric, a knit fabric, and a non-woven fabric.

3. A device according to claim 2, wherein said textile fabric has a weave selected from the group consisting of linen weave, filling-satin weave, and crepe weave.

4. A device according to claim 3, wherein said filling-satin weave has a small repeat.

5. A device according to claim 1, wherein said yarn has more than 1000 twists per meter.

6. A device according to claim 5, wherein said yarn has substantially 2000 to 2400 twists per meter.

7. A device according to claim 1, wherein said textile fabric is comprised of first said yarns and second said yarns, said first yarns having a different direction of twisting than said second yarns.

8. A device according to claim 7, wherein said first yarns are twisted at a change sequence of 1/1 and said second yarns are twisted at a change sequence of 2/2.

9. A device according to claim 1, wherein said size of said fibers is less than 1.8 dtex.

10. A device according to claim 9, wherein said size of said fibers is 1.0 to 1.2 dtex.

11. A device according to claim 1, wherein said size of said yarn is less than 20 tex.

12. A device according to claim 11, wherein said size of said yarn is less than 10 tex.

13. A device according to claim 12, wherein said size of said yarn is between 0.1 and 5.0 tex.

14. A device according to claim 1, further comprising a backing to which backing said textile fabric is attached.

15. A device according to claim 14, wherein said backing is soft and elastic.

16. A device according to claim 14, wherein said textile fabric is quilted onto said backing.

17. A device according to claim 16, wherein said textile fabric is quilted onto said backing in a diamond pattern.

18. A device according to claim 17, wherein said diamond pattern is comprised of diamonds of a side length of 1.0 to 1.5 cm.

19. A device according to claim 1, wherein said hand-held apparatus is selected from the group consisting of a washcloth, a glove, a pad, and a brush.

* * * * *

UNITED STATES PATENT AND TRADEMARK OFFICE
CERTIFICATE OF CORRECTION

PATENT NO.  : 5,439,487
DATED       : August 8, 1995
INVENTOR(S) : Horst Stanitzok It is certified that error appears in the above-identified patent and that said Letters Patent is hereby corrected as shown below:

On the title page: Column 2,
[30]         Foreign Application Priority Data

Feb. 19, 1993 [DE]  Germany ............ 93 02 437.1

Signed and Sealed this

Twelfth Day of December, 1995

Attest:

BRUCE LEHMAN

Attesting Officer

Commissioner of Patents and Trademarks